(12) United States Patent
Leland et al.

(10) Patent No.: US 10,792,189 B2
(45) Date of Patent: Oct. 6, 2020

(54) LOADING TOOL FOR VENTILATION TUBE INSERTER DEVICE

(71) Applicant: Preceptis Medical, Inc., Plymouth, MN (US)

(72) Inventors: Keith J. Leland, Medina, MN (US); James E. Shapland, Vadnais Heights, MN (US)

(73) Assignee: Preceptis Medical, Inc., Maple Grove, MN (US)

( * ) Notice: Subject to any disclaimer, the term of this patent is extended or adjusted under 35 U.S.C. 154(b) by 350 days.

(21) Appl. No.: 15/802,835

(22) Filed: Nov. 3, 2017

(65) Prior Publication Data

US 2018/0140463 A1    May 24, 2018

Related U.S. Application Data

(60) Provisional application No. 62/425,785, filed on Nov. 23, 2016.

(51) Int. Cl.
| A61F 11/00 | (2006.01) |
| A61B 5/06  | (2006.01) |
| A61B 17/24 | (2006.01) |
| A61B 17/00 | (2006.01) |
| A61B 17/34 | (2006.01) |

(52) U.S. Cl.
CPC ............ *A61F 11/002* (2013.01); *A61B 5/065* (2013.01); *A61B 17/24* (2013.01); *A61B 17/3468* (2013.01); *A61B 2017/0053* (2013.01); *A61B 2017/00424* (2013.01); *A61B 2017/00787* (2013.01)

(58) Field of Classification Search
CPC ................ A61B 17/24; A61B 17/3468; A61B 2017/0053; A61F 11/002; A61M 27/002
See application file for complete search history.

(56) References Cited

U.S. PATENT DOCUMENTS

2013/0338678 A1* 12/2013 Loushin ................ A61F 11/002 606/109

* cited by examiner

*Primary Examiner* — Gregory A Anderson
(74) *Attorney, Agent, or Firm* — Leanne Taveggia Farrell; Westman, Champlin & Koehler, P.A.

(57) ABSTRACT

A loading device is configured to load a ventilation tube into an inserter device. The loading device includes a main body and at least one protruding member extending from the main body and terminating at a loading tip. An elongated hollow body has a first end, a second end, an inner wall and an outer wall. The elongated hollow body surrounds the at least one protruding member such that at least a portion of an outer facing surface of the protruding member engages with an inner wall of the elongated hollow body. A ventilation tube engages with the loading tip of the protruding member and is at least partially located within the elongated hollow body.

22 Claims, 13 Drawing Sheets

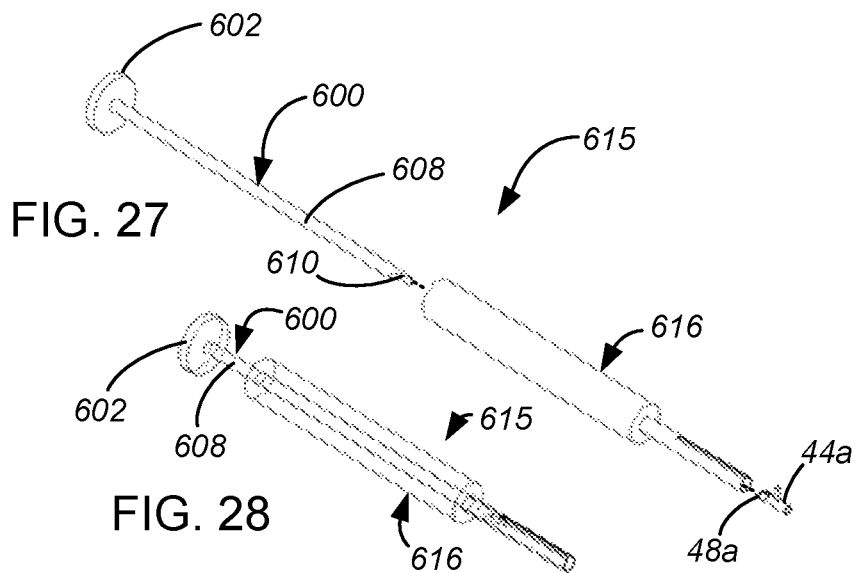
FIG. 27
FIG. 28
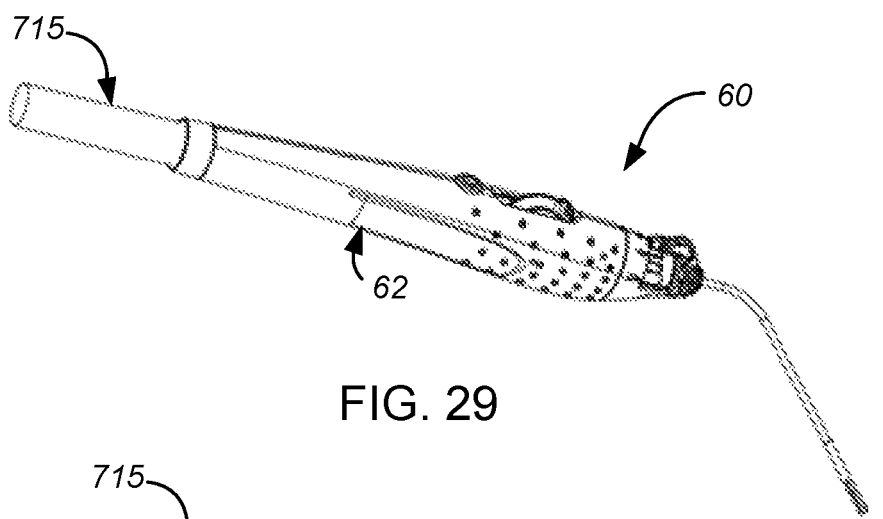
FIG. 29
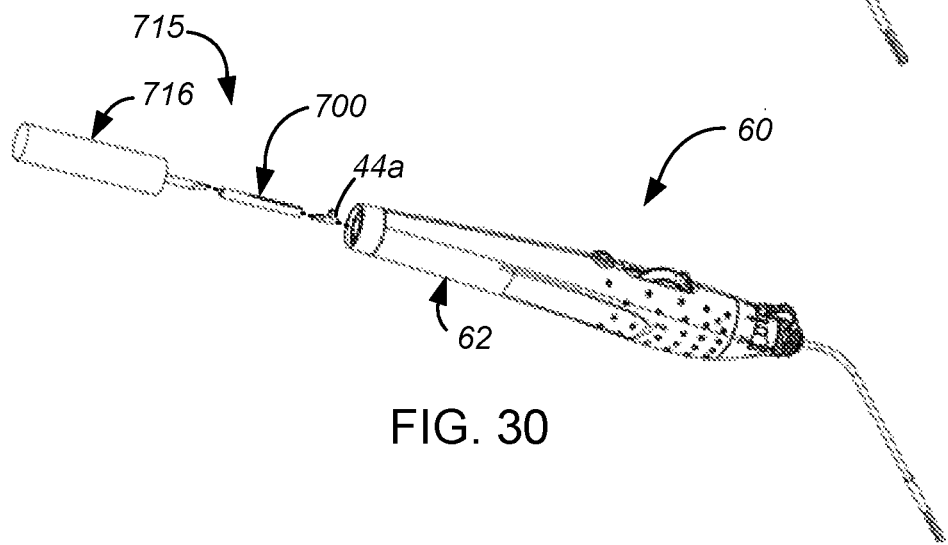
FIG. 30

LOADING TOOL FOR VENTILATION TUBE INSERTER DEVICE

CROSS REFERENCE TO RELATED APPLICATION

The present application is based on and claims the benefit of U.S. provisional patent application Ser. No. 62/425,785, filed Nov. 23, 2016, the content of which is hereby incorporated in its entirety.

BACKGROUND

Placement of middle ear ventilation tubes across the tympanic membrane is a common pediatric surgical procedure for the treatment of middle ear infection or otitis media. Also known as a tympanostomy, the procedure involves creating an incision (i.e., a myringotomy) in the tympanic membrane and placing a tympanostomy tube or ventilation tube in the incision to allow ventilation, pressure equalization and drainage from the middle ear out through the ear canal. The tube can remain in the tympanic membrane for months or years.

Currently, a tube is placed in the tympanic membrane via visualization through a microscope. A sharp blade is used to create the incision and other surgical instruments are used to manipulate the tube into the incision. In the confined space of the ear canal, placement of the tube can be difficult and it is not uncommon for the tube to dislodge from the surgical instrument or for it to accidentally extract from the tympanic membrane before being fully seated, requiring multiple attempts before successful placement is achieved.

Because the middle ear is highly innervated, repeated manipulation of the tympanic membrane is painful enough that patients, especially young children, who make up the majority of tube recipients, require general anesthesia to remain still during the procedure. General anesthesia is costly and poses additional risks.

The discussion above is merely provided for general background information and is not intended to be used as an aid in determining the scope of the claimed subject matter.

SUMMARY

A loading device is configured to load a ventilation tube into an inserter device. The loading device includes a main body and at least one protruding member extending from the main body and terminating at a loading tip. At least one elongated hollow body has a first end, a second end, an inner wall and an outer wall. The elongated hollow body surrounds the protruding member such that at least a portion of an outer facing surface of the protruding member engages with an inner wall of the elongated hollow body. At least one ventilation tube engages with the loading tip of the protruding member and is at least partially located within the elongated hollow body.

A loading device is configured to load a ventilation tube into a distal end of an inserter device. The loading device includes a main body and at least one protruding member extending from the main body and terminating at a loading tip. The loading device further includes at least one elongated hollow body having a first end, a second end, an inner wall and an outer wall. The at least one protruding member is inserted through the second end of the elongated hollow body such that an outer facing surface of the at least one protruding member slidingly engages with an inner wall of the elongated hollow body. The elongated hollow body is configured to hold a ventilation tube in place inside the elongated hollow body so that a medial end of the ventilation tube is in direct contact with the loading tip while the distal end of the inserter device is inserted through the first end of the elongated hollow body.

A method of loading a ventilation tube into a distal end of an inserter device is provided. The method includes holding a ventilation tube in place inside a hollow tubular body having a first end, a second end, an inner wall and an outer wall. A loading tip of a protruding member on a main body engages with the ventilation tube inside the elongated tubular body. A distal end of an inserter device is inserted through a first end of the hollow tubular body to load the ventilation tube inside the distal end of the inserter device.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

FIG. 27 illustrates an exploded perspective view of a loading tool and a loading jig for actively positioning a ventilation tube within an inserter device according to another embodiment.

FIG. 28 illustrates the loading tool and the loading jig of FIG. 27 after the ventilation tube has been loaded into an inserter device.

FIG. 29 illustrates an assembled perspective view of an inserter device with a compartment for holding a loading tool, a loading jig and a preloaded ventilation tube according to one embodiment.

FIG. 30 illustrates an exploded perspective view of the inserter device of FIG. 29 with the compartment for the loading tool, the loading jig and the ventilation tube.

DETAILED DESCRIPTION

The loading devices described herein are configured to aid a user or manufacturer in manually loading a ventilation tube into a distal end of an inserter device, or configured to hold a ventilation tube or tubes in a pre-loaded configuration such that the user can more easily load them into an inserter device. The loading devices align the ventilation tube with the inserter device, deforms the ventilation tube or ventilation tube flange(s) to correctly position the ventilation tube in the inserter device, and releases the ventilation tube into the correct position in the inserter device.

Figure 1:
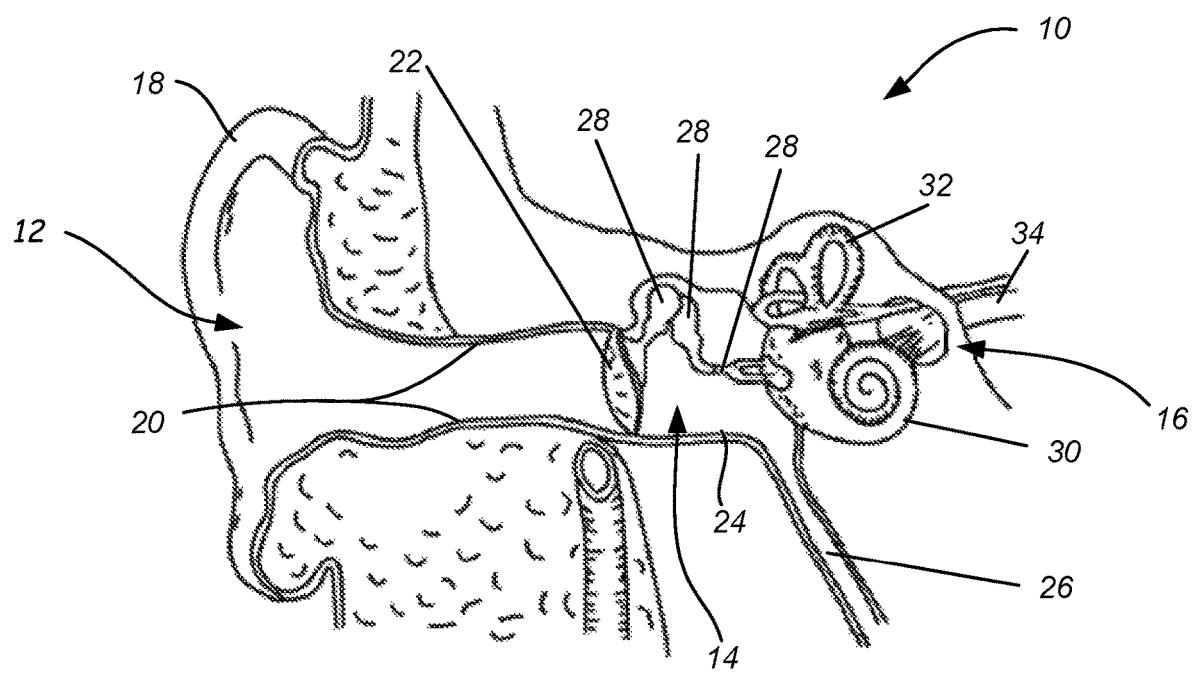
FIG. 1 is a simplified diagrammatic view of a system of organs in an ear.

FIG. 1 is a simplified diagrammatic view of a system of organs in an ear 10 of a body that enables a person to detect sound. Ear 10 includes an outer ear 12, a middle ear 14 and an inner ear 16. Outer ear 12 collects sound and includes the pinna 18, the ear canal 20 and an outer most layer of the ear drum or tympanic membrane 22. Pinna 18 helps direct sound through ear canal 20 to tympanic membrane 22. Middle ear 14 includes an air-filled cavity 24 having an opening for the Eustachian tube 26 that is located behind tympanic membrane 22. Middle ear 14 also includes ossicles bones 28. Inner ear 16 includes the fluid-filled cochlea 30 and the semicircular canals 32. Cochlea 30 is the auditory portion of the inner ear, while semicircular canals 32 are attuned to both gravity and motion. The ossicles bones 28 transmit sound from the air in cavity 24 to cochlea 30. Fluid in cochlea 30 moves in response to the vibrations coming from middle ear 14. The motion of the fluid is converted to electrical impulses, which travel along the auditory nerve 34 to structures in the brainstem for further processing. Eustachian tube 26 couples cavity 24 of middle ear 14 to the nose and mouth of a human. In a normal state, Eustachian tube 26 is collapsed. However, Eustachian tube 26 can open and close to equalize pressure in cavity 24.

Ventilation tubes are placed across the tympanic membrane (TM) 22 to treat chronic otitis media primarily in infants and children. It is estimated that over a million such procedures are annually performed in the United States. To facilitate ventilation tube placement, inserter devices have been developed to enhance the safety and reduce the trauma associated with the procedure. Ventilation tubes come in a variety of designs and materials. However, all ventilation tubes include a hollow body or lumen and some include a medial flange or member protruding from the medial end of the hollow body to minimize the potential for dislodgement of the tube. A medial flange is a flange located internal to TM 22 when the ventilation tube is located in TM 22. A lateral flange is a flange located external to TM 22 when the ventilation tube is located in TM 22.

Figure 2:
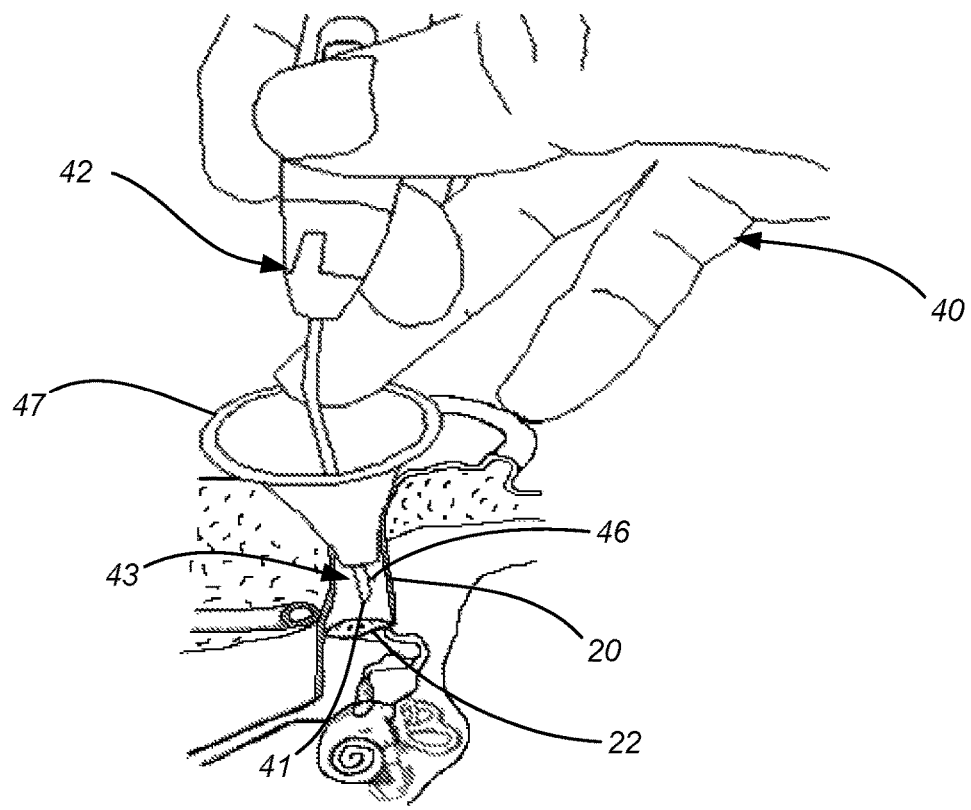
FIG. 2 illustrates a surgeon's hand positioning an inserter device into an ear canal of an ear to insert a ventilation tube into a tympanic membrane.

FIG. 2 illustrates a physician's hand 40 positioning an inserter device 42 inside ear canal 20 of ear 10 using a speculum 47 to straighten and hold open the ear canal. As shown in FIG. 2, a distal end 41 and distal portion 43 of inserter device 42 is positioned in ear canal 20 and adjacent to tympanic membrane 22. Distal end 41 of inserter device 42 then makes an incision in tympanic membrane 22 and a ventilation tube (located within the distal end of the inserter device where a lateral flange 46 of ventilation tube protrudes through a slot in a cutting sheath in the distal end of the inserter device 42) is placed across tympanic membrane 22 through the incision. The ventilation tube is then deployed by inserter device 42 across tympanic membrane 22 by, for example, pulling back on the cutting sheath. Other deployment means are possible including pushing the tube out of the distal end of inserter device 42.

Various embodiments of and examples of ventilation tubes are illustrated in FIGS. 3-7 that may be used with the inserter device 42. In one embodiment, ventilation tubes illustrated in FIGS. 3-7 can be flexible in material so that they can be constrained into an undeployed state and unconstrained into a deployed state. In other embodiments, the ventilation tube may be made of a rigid material, for example, tube 44b of FIG. 4 can be made of a rigid material.

Figure 3:
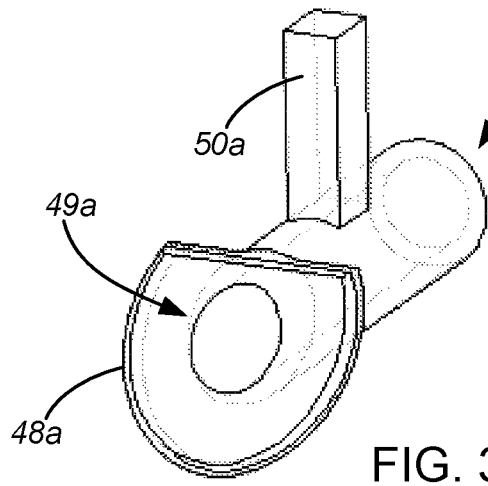
FIGS. 3-7 illustrate of various embodiments of ventilation tubes in the deployed state.
Figure 4:
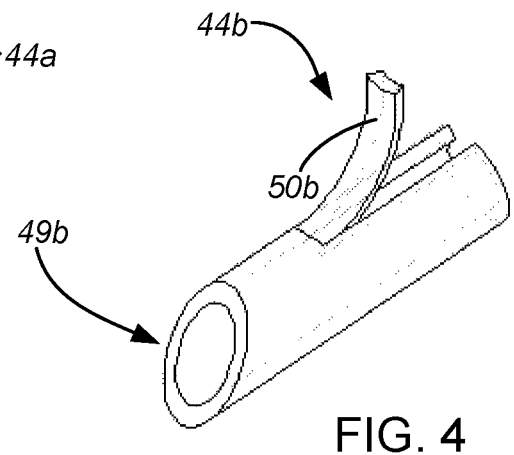
Figure 5:
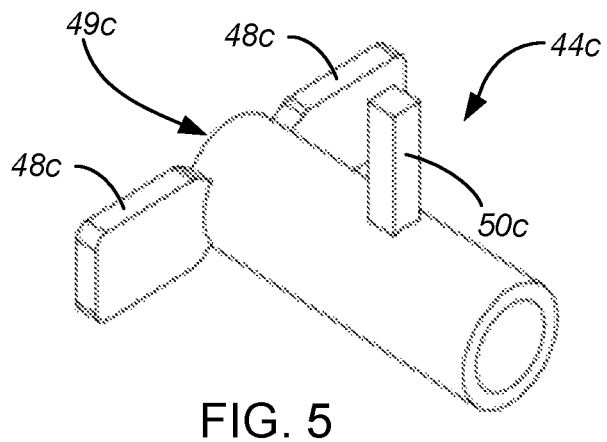
Figure 6:
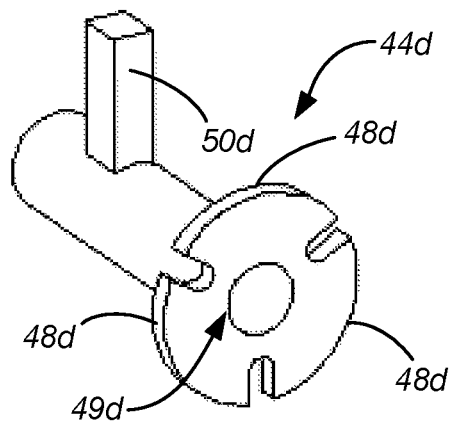
Figure 7:
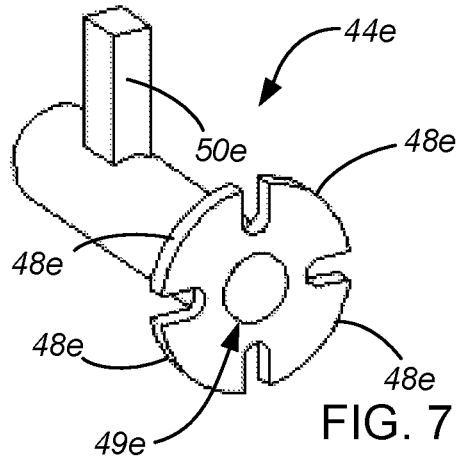

FIG. 3 illustrates a perspective view of a ventilation tube 44a in its deployed state. As shown, a medial flange 48a is located at the medial end 49a of tube 44a. Ventilation tube 44a also includes a lateral flange 50a to aid in visualization of the tube during insertion and to prevent medialization of the tube into the middle ear space. FIG. 4 illustrates a perspective view of a ventilation tube 44b with no medial flange at medial end 49b, but incorporating a lateral flange 50b for visualization. FIGS. 5, 6 and 7 shows embodiments of ventilation tubes 44c, 44d and 44e, respectively, with two, three and four medial flanges at medial ends 49c, 49d and 49e, respectively, and each ventilation tube 44c, 44d and 44e having a lateral flange 50c, 50d and 50e. As illustrated, FIGS. 5, 6 and 7 include instances of multiple medial flanges and the multiple flanges are shown to be of substantially equal size. However, loading devices for locating a ventilation tube in an inserter device are suitable for use with multi-flanged medial end embodiments where flange sizes are not equal are also possible. In addition, while only a single lateral flange is illustrated in FIGS. 3-7, in other embodiments, ventilation tubes can have two or more lateral flanges. In these embodiments, one of the lateral flanges acts as a deployed visualization tab and the remaining lateral flanges can be deformed/constrained. Other tube embodiments that could be loaded by an inserter device include vent tube with only one or more medial flanges, with only one or more lateral flanges or without a medial and or lateral flange.

As illustrated in FIG. 3, ventilation tube 44a includes medial flange 48a and medial end 49a that are beveled at an angle relative to the hollow body of ventilation tube 44a. The beveled medial flange 48a and beveled medial end 49a means the bottom of the hollow body of ventilation tube 44a is greater in length than the top of the hollow body of ventilation tube 44a.

Figure 8:
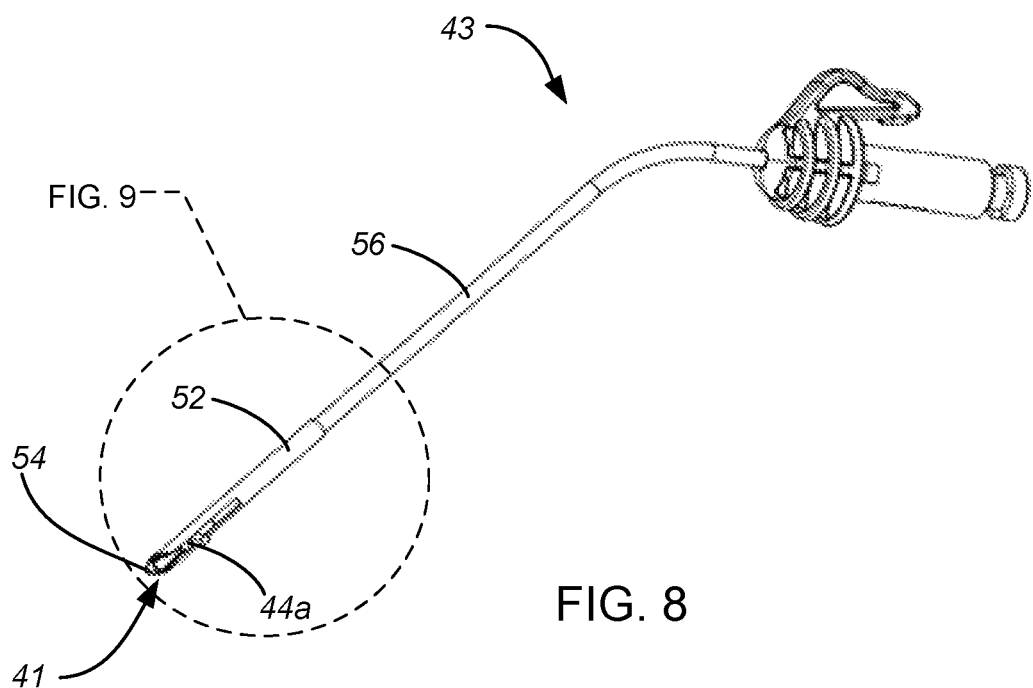
FIG. 8 illustrates a perspective view of a ventilation tube in the undeployed state constrained in a distal portion of an inserter device.
Figure 9:
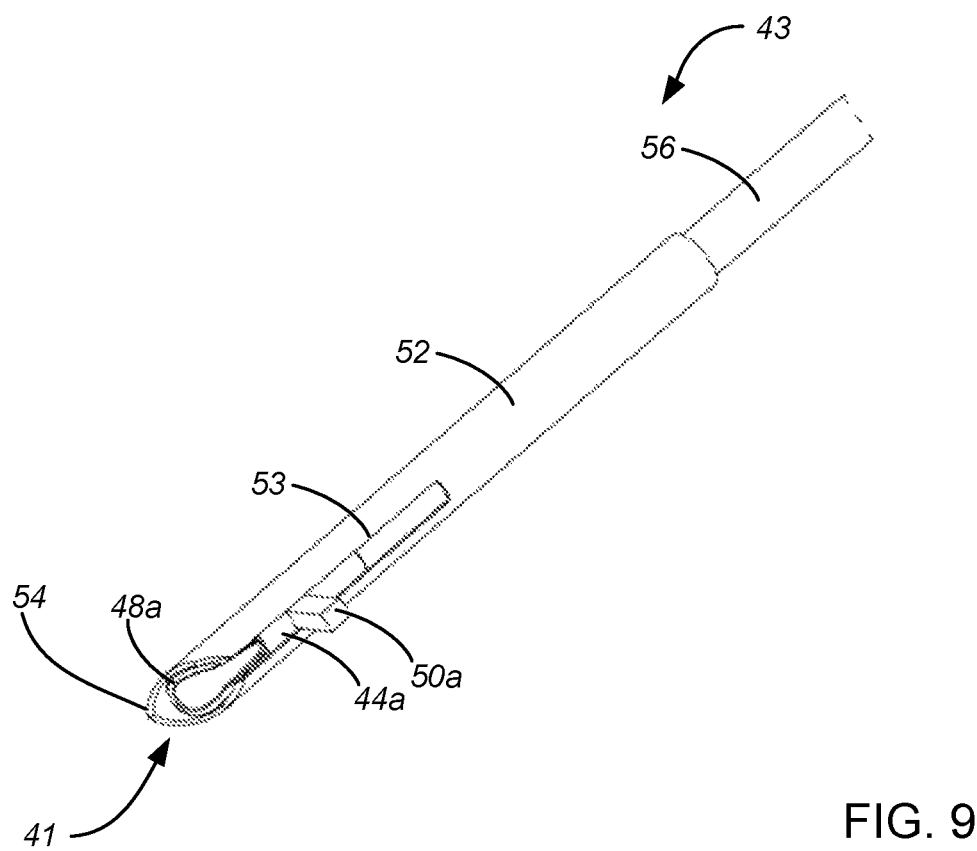
FIG. 9 is an enlarged view of the distal end of the distal portion in FIG. 8.

FIG. 8 illustrates a perspective view of ventilation tube 44a constrained in a distal portion 43 of an inserter device and therefore in the undeployed state. FIG. 9 is an enlarged view of the distal end of distal portion 43 in FIG. 8. Prior to use, medial flange 48a of ventilation tube 44a or medial flanges 48c, 48d and 48e of ventilation tubes 44c, 44d and 44e are positioned or loaded into a cutting sheath 52 at distal end 41 of distal portion 43 of an inserter device and therefore deformed into an undeployed state. In FIGS. 8 and 9, ventilation tube 44a is illustrated deformed within cutting sheath 52 at distal end 41 of distal portion 43 with lateral flange 50a protruding through a slot 53 in cutting sheath 52. However, it should be realized that any of ventilation tubes 44b-44e can be used within cutting sheath 52.

Cutting edge 54 of cutting sheath 52 makes an incision in the tympanic membrane. Cutting sheath 52 as well as ventilation tube 44a are then positioned across the tympanic membrane. Cutting sheath 52 is pulled back along positioning rod 56 and ventilation tube 44a is then free to deploy so that medial flange 48a assumes its non-deformed or deployed state. In the alternative, rod 56 can push ventilation tube 44a into the tympanic membrane and ventilation tube 44a assumes its non-deformed or deployed state. The loading of the ventilation tube into cutting sheath 52 of the inserter device can be performed by the manufacturer, the physician or end user at the time of the procedure and components for doing so are described in detail below.

Figure 10:
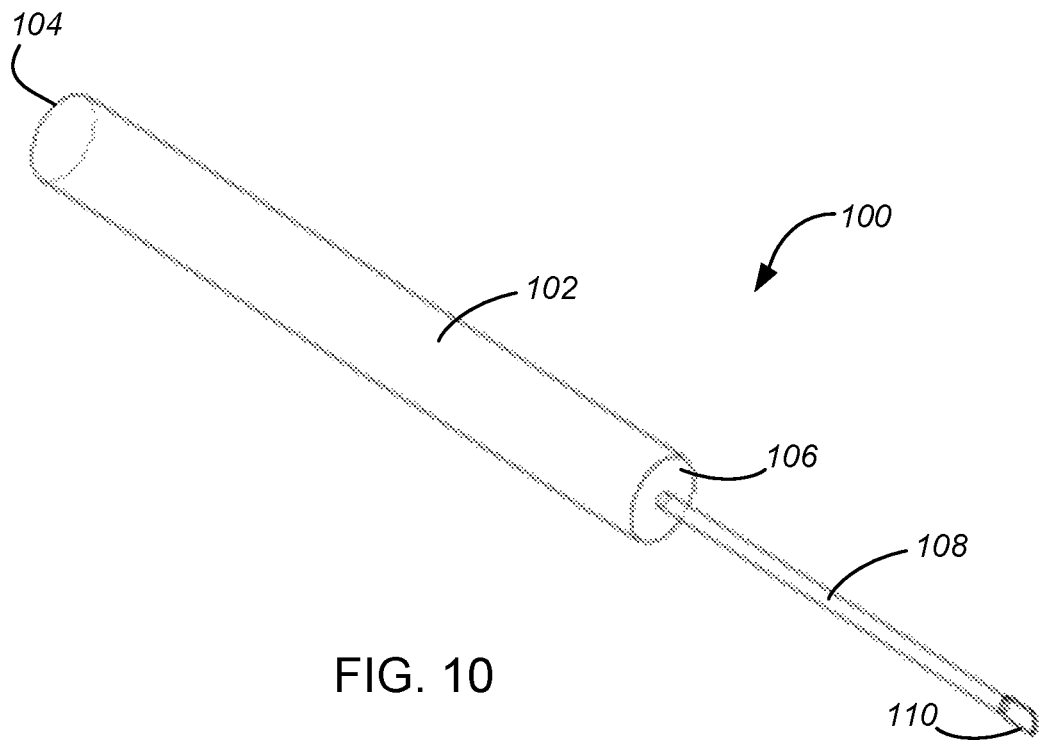
FIG. 10 is a perspective view of one embodiment of a loading tool for loading a ventilation tube into the inserter device illustrated in FIGS. 8 and 9.

FIG. 10 illustrates a perspective view of one embodiment of a loading tool 100 for loading a ventilation tube into cutting sheath 52 illustrated in FIGS. 8 and 9. Loading tool 100 includes a main body or handle 102 having a first end 104 and a second end 106. A protruding member 108 extends from second end 106 of main body 102 and terminates at and includes a spatulated or chiseled end 108 configured to manipulate ventilation tube 44a into cutting sheath 52. After pushing ventilation tube 44a up into cutting sheath 52 to leave ventilation tube 44a in place, spatulated end 110 is configured to be thin enough to allow it to fit through slot 53 in cutting sheath 52. In other words, loading tool 100 and ventilation tube 44a are advanced axially into cutting sheath 52 and after ventilation tube 44a is loaded, loading tool 100 is removed radially through slot 53 in cutting sheath 52 to prevent ventilation tube 44a from being dislodged or pulled back out of cutting sheath 52 when loading tool 100 is removed. Therefore, slot 53 allows lateral flange 50a to protrude through and act as a visual tab to determine the position of the ventilation tube 44a with respect to tympanic membrane 22, however, slot 53 also acts as an outlet for removing spatulated end 110 from cutting sheath 52. Other shapes other than a spatulate shape are also possible as long as the tip geometry is small enough to fit inside cutting sheath 52 and fit in or through slot 53 of cutting sheath 52. Examples includes a bendable wire bent into a shape such as a hook, loop or "U" shape.

Figure 11:
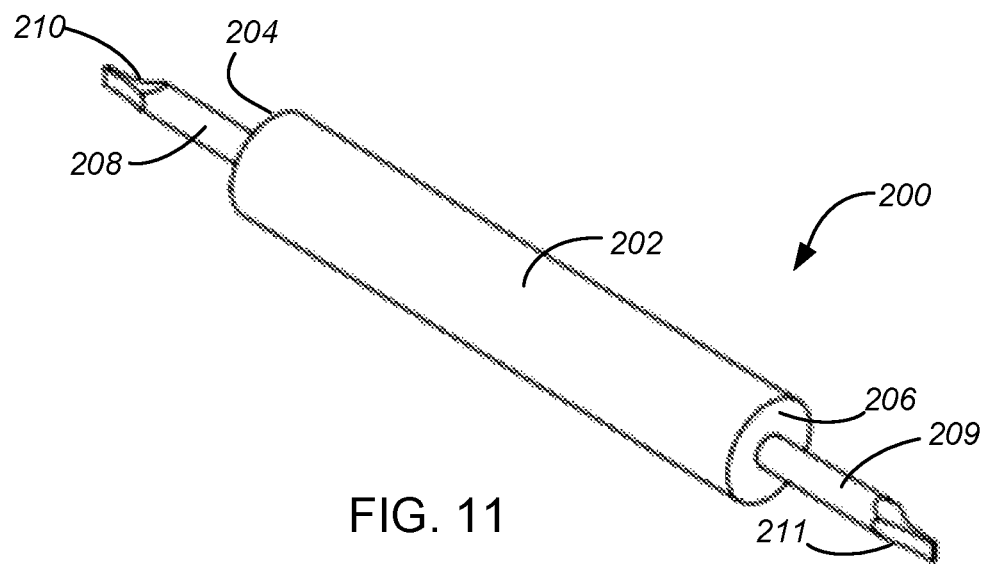
FIG. 11 is a bottom perspective view of another embodiment of a loading tool for loading a ventilation tube into the inserter device illustrated in FIGS. 8 and 9.
Figure 12:
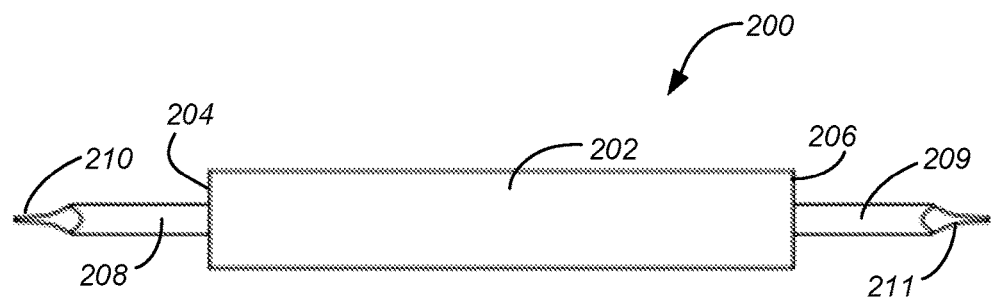
FIG. 12 is a bottom view of FIG. 11.
Figure 13:
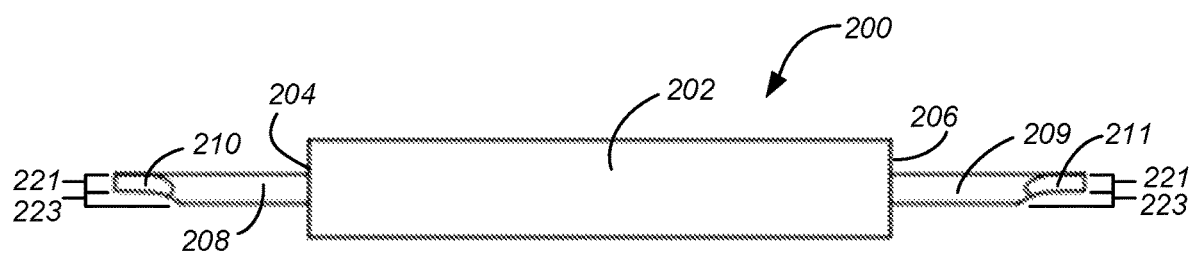
FIG. 13 is a side view of FIG. 11.
Figure 14:
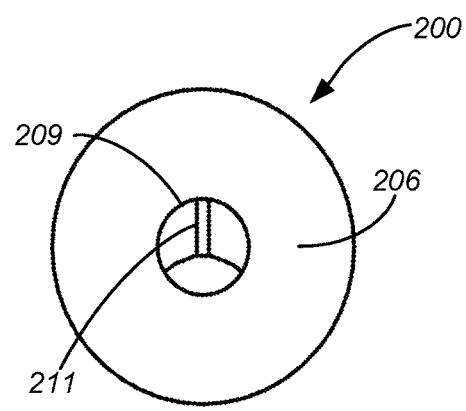
FIG. 14 is an enlarged end view of FIG. 11.

FIG. 11 illustrates a bottom perspective view of another embodiment of a loading tool 200 for loading a ventilation tube into cutting sheath 52 illustrated in FIGS. 8 and 9. FIG. 12 is bottom view of loading tool 200, FIG. 13 is a side view of loading tool 200 and FIG. 14 is an end view of loading tool 200. Loading tool 200 includes a main body or handle 202 having a first end 204 and a second end 206. Loading tool 200 also includes a first protruding member 208 that extends from first end 204 and terminates at and includes a first loading tip 210 and a second protruding member 209 that protrudes from second end 206 and terminates at and includes a second loading tip 211. While FIGS. 11, 12, and 13 illustrate a substantially similar loading tip on each opposing protruding end, it is possible that a loading tool could have a single protruding member with a single loading tip, or could include different loading tip geometries on opposing ends. Each loading tip 210 and 211 includes a narrowed/spatulated end configured to manipulate a ventilation tube into cutting sheath 52 such that the medial flange of the ventilation tube is compressed while the ventilation tube is advanced into cutting sheath 52. The narrowed/spatulated ends of loading tips 210 and 211 allow loading tool 200 to interface with slot 53 in cutting sheath 52 during loading, allowing the ventilation tube to be loaded axially and the narrowed/spatulated end subsequently removed through slot 53 of cutting sheath 52 radially or axially without disrupting the loaded ventilation tube.

Spatulated ends of loading tips 210 and 211 include a top section 221 and a bottom section 223 (FIG. 13). Top section 221 includes a straight blunt end that is substantially perpendicular to the axis to which protruding members 208 and 209 extend along. Bottom section 223 includes an arcuate cutout or curved taper. This particular shape of spatulated ends of loading tips 210 and 211 will be discussed in more detail below in regards to ventilation tubes and the distal end of distal portion 43 of an inserter device such as the distal end illustrated in FIGS. 8 and 9.

Figure 15:
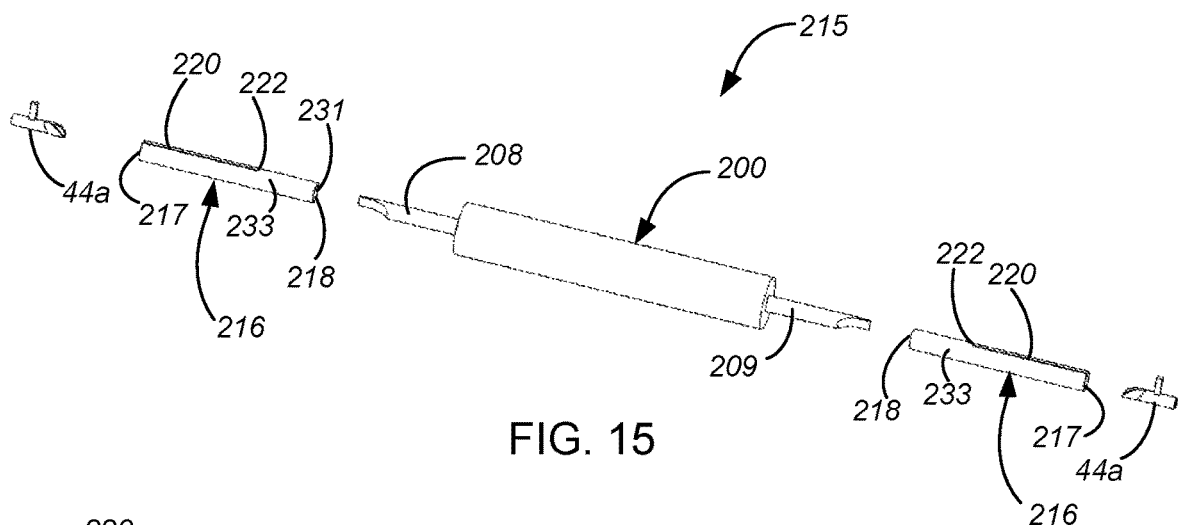
FIG. 15 illustrates an exploded perspective view of a loading device including a pair of loading jigs that mate with the loading tool illustrated in FIGS. 11-14 to each hold a ventilation tube in a preloaded configuration.
Figure 16:
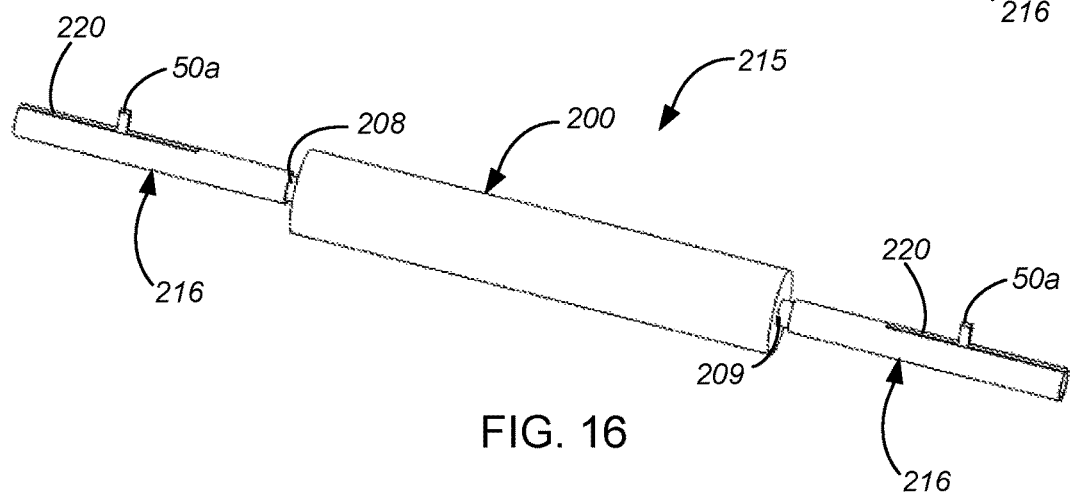
FIG. 16 illustrates a perspective view of the loading device illustrated in FIG. 15 as assembled.
Figure 17:
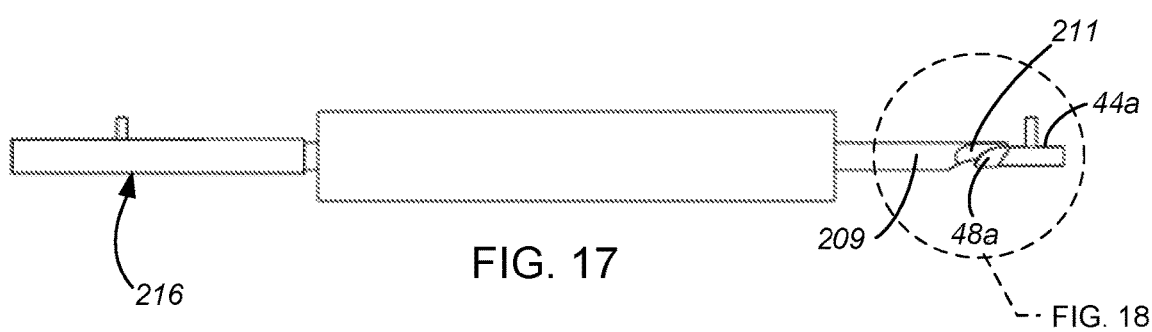
FIG. 17 illustrates a side view of the loading device illustrated in FIG. 16 with one of the loading jigs removed.

FIG. 15 illustrates an exploded perspective view of a loading device 215. FIG. 16 illustrates a perspective view of loading device 215 as assembled and preloaded with two ventilation tubes 44a. FIG. 17 illustrates the assembled view of FIG. 16 with one of the loading jigs 216 removed to illustrate the engagement between a loading tip of a protruding member and ventilation tube 44a. Loading device 215 includes a pair of loading jigs or packages 216 that mate with loading tool 200 shown in FIGS. 11-14 to hold ventilation tubes, such as ventilation tubes 44a, in a preloaded configuration. While FIGS. 15 and 16 illustrate loading device 215 with two loading jigs 216, one mated with each of the protruding members 208 and 209, it is possible for loading device 215 to include only one protruding member that mates with only one loading jig. The preloaded configuration shown in FIG. 16 allows an end-user to more easily load or reload tubes into an inserter device, and, in one embodiment, can be used to load tubes directly into an inserter device.

Each loading jig 216 includes an elongated hollow body having a first end 217, a second end 218, an inner wall 231 and an outer wall 233. Each loading jig 216 also includes a slot 220 that extends through inner wall 231 and outer wall 233 and runs from first end 217 along a partial length of the elongated hollow body and terminates at a terminating end 222 that is spaced apart from second end 218. The elongated hollow body of loading jig 216, in one embodiment, is made from a transparent polymer to allow direct visualization of a preloaded ventilation tube and to aid in positioning the device during loading/reloading. The polymer tubing of loading jig 216 has an inner wall or lumen diameter that is slightly larger than the outer diameter of cutting sheath 52 and an inner wall or lumen diameter that is also slightly larger than the outer diameters of protruding members 208 and 209 of loading tool 200. In order to account for normal variations, or dimensional tolerances, in tubing diameter, protruding members 208 and 209 of loading tool 200 may include a tapered diameter, or a tapered rib to ensure that loading jig 216 is capable of fitting over the protruding member while still allowing for a frictional interference fit between the two pieces along a portion of their interface.

Figure 18:
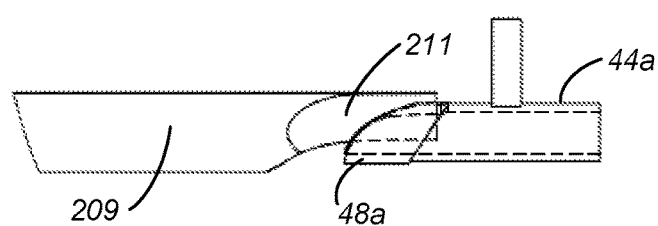
FIG. 18 is an enlarged view of the loading tip in FIG. 17 engaged with a ventilation tube.

In FIG. 16, each loading jig 216 of loading device 215 is sleeved over or mated with protruding member 208 or 209 by slidingly engaging an outer facing surface of protruding member 208 or 209 with inner wall 231 of the elongated hollow body. FIGS. 17 and 18 illustrate how the preloaded ventilation tubes 44a engage with spatulated tips 210 and 211 by showing loading device 215 in FIG. 16 with one of the loading jigs 216 removed. In particular, the upper portion of medial flange 48a of ventilation tube 44a is engaged with top section 221 (FIG. 13) of spatulated tip 211. The lower portion of medial flange 48a of ventilation tube 44a is positioned adjacent to the arcuate cutout of bottom section 223 (FIG. 13) of spatulated tip 211. The arcuate cutout of bottom section 223 makes space for accommodating a bottom of medial flange 48a. In addition, lateral flanges 50a of each ventilation tube 44a protrudes through each slot 220 in each loading jig 216 similar to how lateral flange 50a protrudes through slot 53 in cutting sheath 52.

Figure 19:
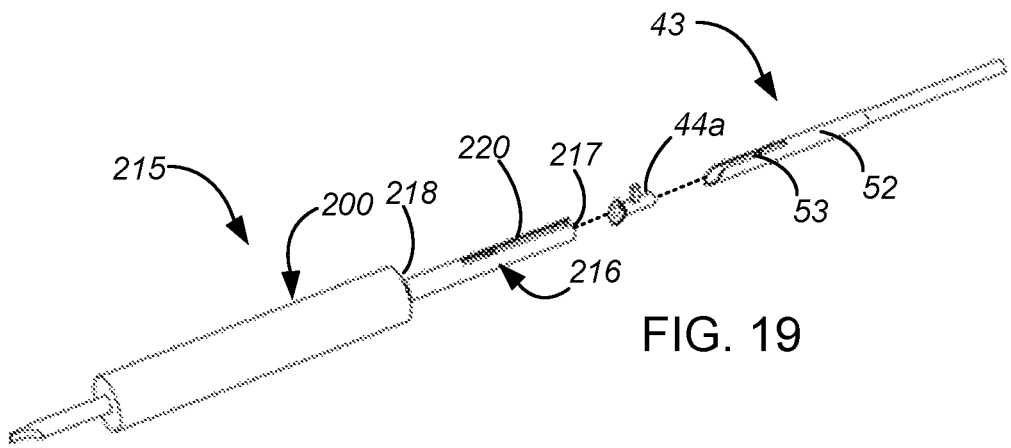
FIGS. 19-22 illustrate perspective views of the progressive loading of the ventilation tube into the inserter device using the assembled loading device illustrated in FIG. 16.
Figure 20:
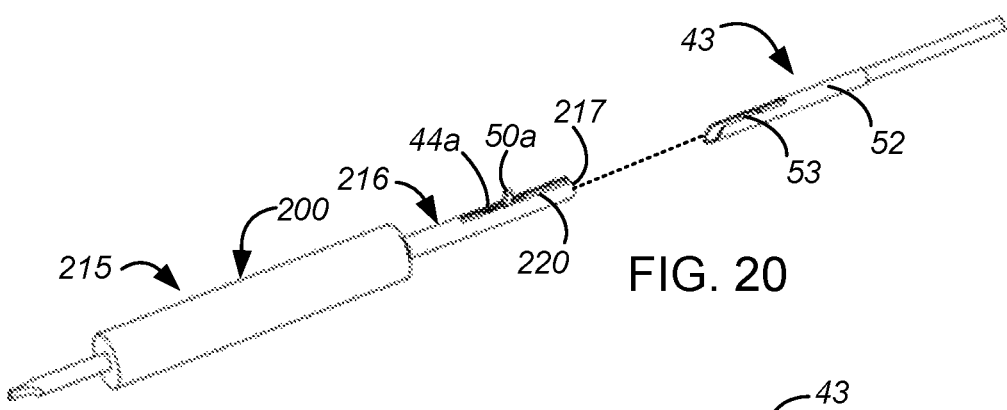
Figure 21:
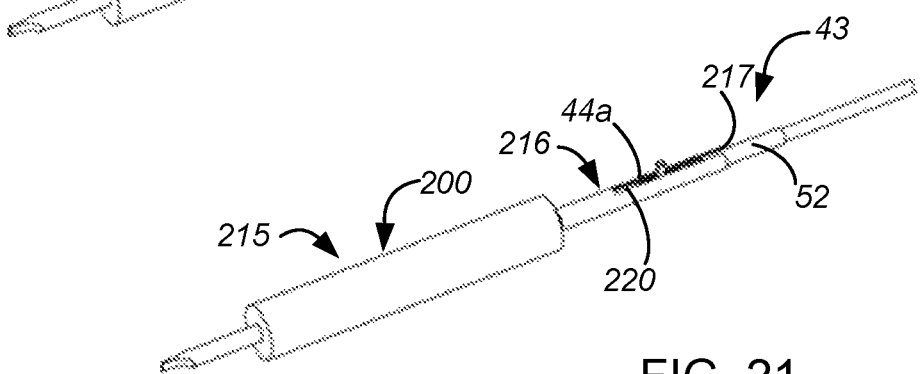
Figure 22:
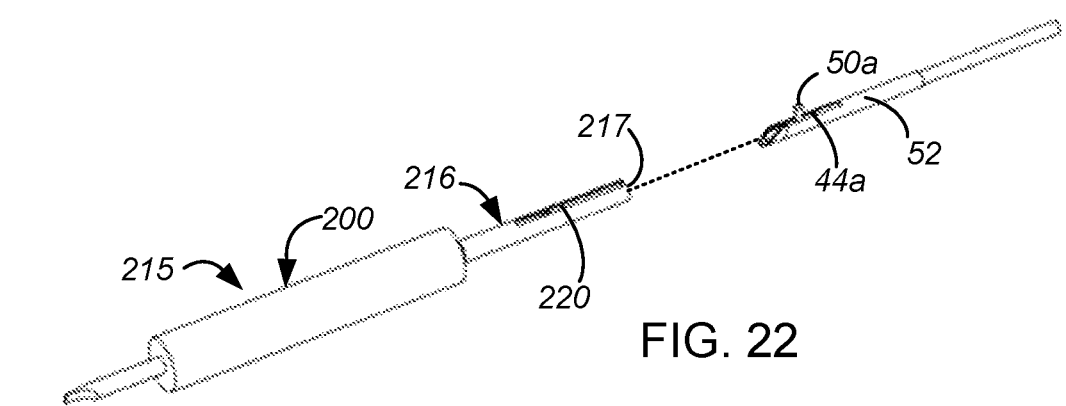

FIGS. 19-22 illustrate perspective views of the progression of loading ventilation tube 44a into a distal portion 43 of an inserter device using loading device 215 shown in FIGS. 15 and 16, but with a single loading jig 216. In FIG. 19, ventilation tube 44a is shown exploded from a preloaded position inside of loading jig 216 and a distal end of distal portion 43 of an inserter device is in position to be loaded with ventilation tube 44a. In FIG. 20, ventilation tube 44a is shown preloaded in loading jig 216, which includes medial flange 48a being engaged with spatulated tip 210 of loading tool 200 such that in a preloaded configuration, ventilation tube 44a is held in a compressed configuration similar to the configuration it assumes when loaded into cutting sheath 52. As shown in FIG. 21, a user can then use loading tool 200 and loading jig 216 to load or reload ventilation tube 44a into the distal end of distal portion 43 of an inserter device. In this embodiment, cutting sheath 52 is inserted into loading jig 216 at first end 217 such that slot 53 in cutting sheath 52 aligns with slot 220 in loading jig 216 and with lateral flange 50a. Distal end of distal portion 43 of the inserter device is manually advanced, and thereby cutting sheath 52 is manually advanced through first end 217 and the elongated hollow body of loading jig 216 until the internal diameter of cutting sheath 52 is positioned below the arcuate cutout of bottom section 223 (FIG. 13) of spatulated tip 210 and therefore also below the bottom portion of medial flange 48a. A friction between the bottom portion of medial flange 48a and inner wall 231 of the elongated hollow tube of loading jig 216 is replaced by a friction between the bottom portion of medial flange 48a and the inner diameter of cutting sheath 52. As shown in FIG. 22, this exchange of friction allows cutting sheath 52 to take ventilation tube 44a with it when cutting sheath 52 is retracted from loading jig 216 thereby loading ventilation tube 44a into cutting sheath 52.

In one embodiment, the use of clear or translucent/non-opaque polymer tubing for loading jig 216 can make loading easier, and the use of a slippery (PTFE or similar) tubing contributes to a reduction in friction between the cutting sheath and the loading jig during the loading process, and a softer tubing also prevents dulling of the cutting edges of cutting sheath 52. As previously described, loading tool 200 could be double ended or single ended, or could have one end with a pre-loaded ventilation tube for reloading, and one end that is bare.

Figure 23:
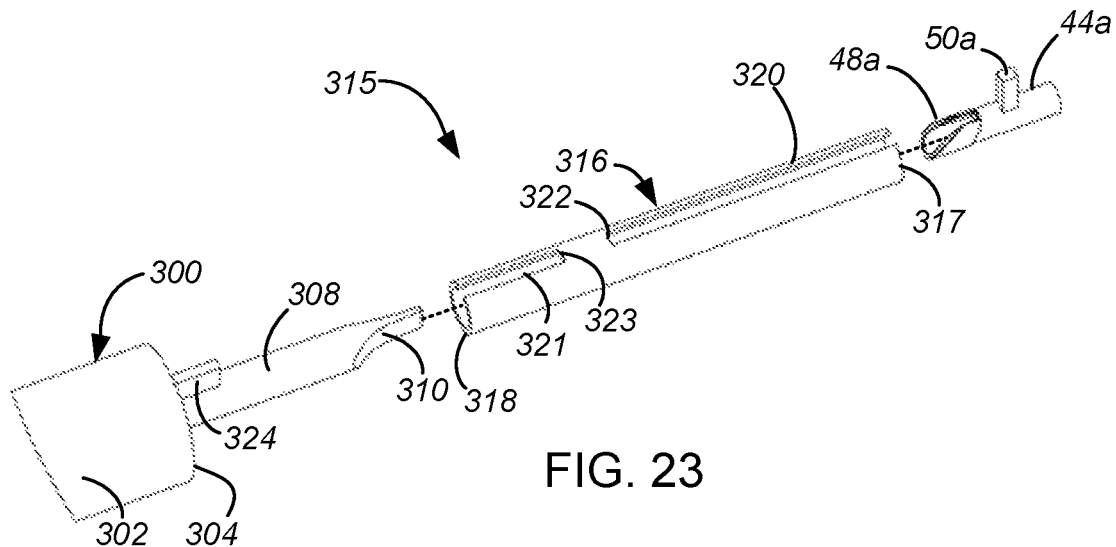
FIG. 23 illustrates an exploded perspective view of a portion of a loading tool, a loading jig, and a ventilation tube, where the loading tool has a register element to align the tool and jig.

FIG. 23 is an enlarged exploded view of a portion of a loading device 315 according to another embodiment. Loading device 315 includes a loading jig 316 having a first slot 320 and a second slot 321. First slot 320 extends from a first end 317 of loading jig 316 to a terminating point 322. Second slot 321 extends from a second end 318 of loading jig 316 to a terminating point 323 that is spaced apart from terminating point 322 of first slot 320. While FIG. 23 illustrates slots 320 and 321 as being collinear, it should be realized that slot 321 can be located along a side of jig 316 that is not aligned with slot 320. For example, slot 321 can be located 180 degrees opposite or anywhere along jig 316. Loading device 315 also includes loading tool 300 having protruding member 308 with a narrowed/spatulated loading tip 310. Located on protruding member 308 is a registration element 324 that interfaces or engages with slot 321 in loading jig 316 to orient the jig tubing relative to spatulated loading tip 310. Registration element 324 protrudes radially from protruding member 308 and is located adjacent to first end 304 of main body 302 of loading tool 300. Registration element 324 provides a means of registering loading jig 316 with loading tool 300. For correct orientation of all of the elements of loading device 315, including ventilation tube 44a being oriented with the distal end of distal portion 43 of the inserter device during reloading, it is desirable to have positive alignment between all of the elements. Slot 320 of loading jig 316 interfaces with lateral flange 50a on ventilation tube 44a then orients ventilation tube 44a relative to the spatulated loading tip 310 of loading tool 300 such that medial flange 48a is compressed into the correct orientation. Lateral flange 50a then provides a physical and visual landmark for orientating cutting sheath 52 of the inserter device with loading device 315 such that ventilation tube 44a is loaded into cutting sheath 52 correctly. While slots 320 and 321 in loading jig 316 are shown as two distinct, separate slots, it is possible that other embodiment could also consist of a single slot, or slit, running the entire length of the polymer tubing of loading jig 316.

Figure 24:
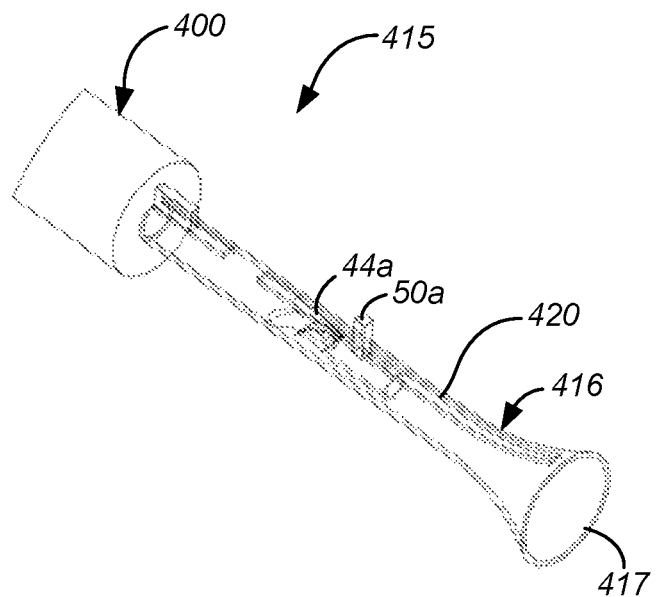
FIG. 24 illustrates a perspective view of a portion of an assembled loading tool, a loading jig with a flanged end and a ventilation tube according to another embodiment.

FIG. 24 is an enlarged view of a portion of a loading device 415 according to another embodiment. Loading device 415 includes a tapered or cone-like lead-in at first end 417 of loading jig 416 to help in registering loading device 415 with cutting sheath 52 of the inserter device during the reloading process. By providing a tapered lead in at first end 417, aligning cutting sheath 52 with loading tool 400 can be more easily accomplished. Slot 420 in loading jig 416, which allows lateral flange or vis-tab 50a of ventilation tube 44a to exit loading device 415, may or may not extend fully to the end of the tapered lead in element. In FIG. 24, it does not extend to first end 417.

Figure 25:
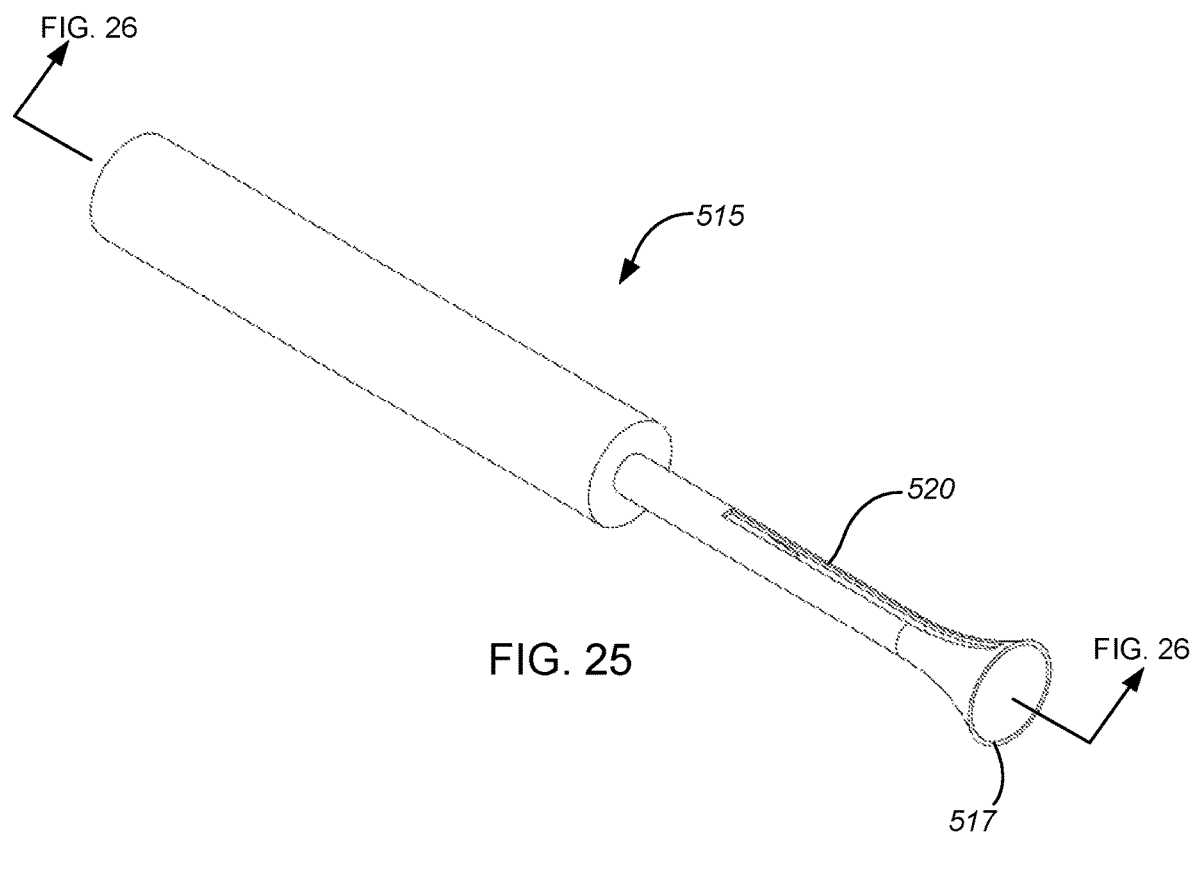
FIG. 25 illustrates a perspective view of a monolithic loading device according to another embodiment.
Figure 26:
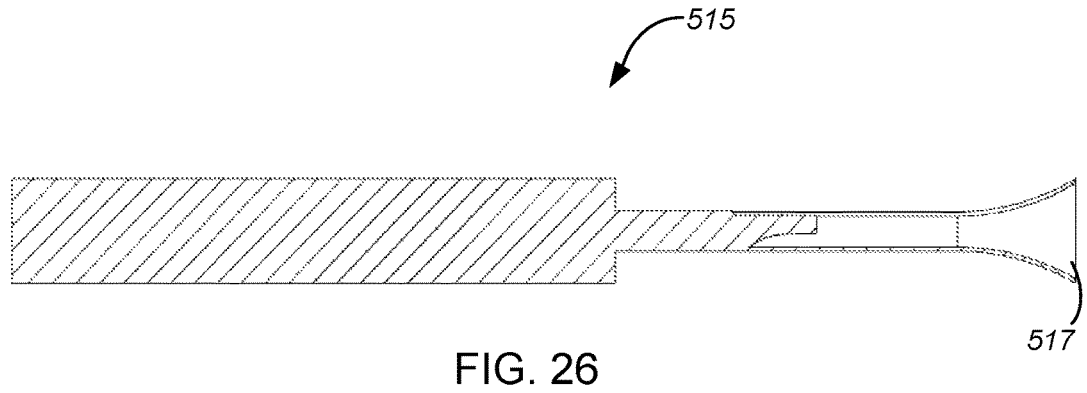
FIG. 26 is a section view of the loading device of FIG. 25 taken through the section line indicated in FIG. 25.

Further, the loading jig and elements of a loading device could be manufactured as separate pieces, or as a single molded or bonded pieces as illustrated in FIGS. 25 and 26. FIG. 25 illustrates a perspective view of a monolithic loading device 515 according to one embodiment. FIG. 26 is a section view of loading device 515 taken through the section line indicated in FIG. 25. Loading device 515 includes a tapered or cone-like lead-in at first end 517 to help in registering loading device 515 with cutting sheath 52 of the inserter device during the reloading process. By providing a tapered lead in at first end 517, aligning cutting sheath 52 with loading device 515 can be more easily accomplished. Slot 520, which allows lateral flange or vis-tab 50a of ventilation tube 44a to exit loading device 515, may or may not extend fully to the end of the tapered lead in element. In FIG. 26, it does not extend to first end 517.

FIG. 27 illustrates an exploded perspective view of a loading device 615 according to yet another embodiment. FIG. 28 illustrates an assembled view of loading device 615 without ventilation tube 44a. Loading device 615 includes loading tool 600 and a loading jig 616. Loading tool 600 has a protruding member 608 that protrudes from a main body 602. Protruding member 608 includes a loading tip 610 having a narrowed/spatulated end such that medial flange 48a of ventilation tube 44a can be compressed and slid into cutting sheath 52. A main body 602 of loading tool 600 acts like a handle and the entirety of loading tool 600 is a movable insertion element that allows the user to 'push' ventilation tube 44a out of loading jig 516 and into cutting sheath 52 of the inserter device. Like other described embodiments of loading devices, ventilation tube 44a in FIG. 28 is held in place in loading jig 616 via friction between the compressed medial flange 48a and the tubing of loading jib 616. When cutting sheath 52 is introduced into loading jig and medial flange 48a is transferred into cutting sheath 52, the friction between ventilation tube 44a and cutting sheath 52 allows ventilation tube 44a to be removed from loading jig 616 and left in cutting sheath 52 due to the friction between ventilation tube 44a and cutting sheath 52. In instances where these frictional forces are not sufficient, or where tube geometries may require it, like in loading device 615, loading device 615 includes an active element (i.e., loading tool 600) to eject ventilation tube 44a from loading jig 616 into cutting sheath 52 such that frictional forces are not relied upon.

FIG. 29 illustrates a perspective view of an inserter device 60 with a loading device, such as a loading device 715, integrated into a handle 62. FIG. 30 illustrates an exploded perspective view of loading device 715 exploded from inserter device 60. To simplify loading by an end user, incorporating loading device 715 or a preloaded loading device 715 into inserter device 60, as is shown in the exploded FIG. 30 view, would allow a clinician or user to quickly and efficiently locate and use loading device 715. Loading device 715 could be physically part of the handle as shown with a friction or snap fit to hold it in place until such time as it needs to be removed for use. Conversely, loading device 715 could be an integral part of handle 62, and could be used to reload a removable tip assembly that is removed from the front of inserter device 60 for loading.

Figure 31:
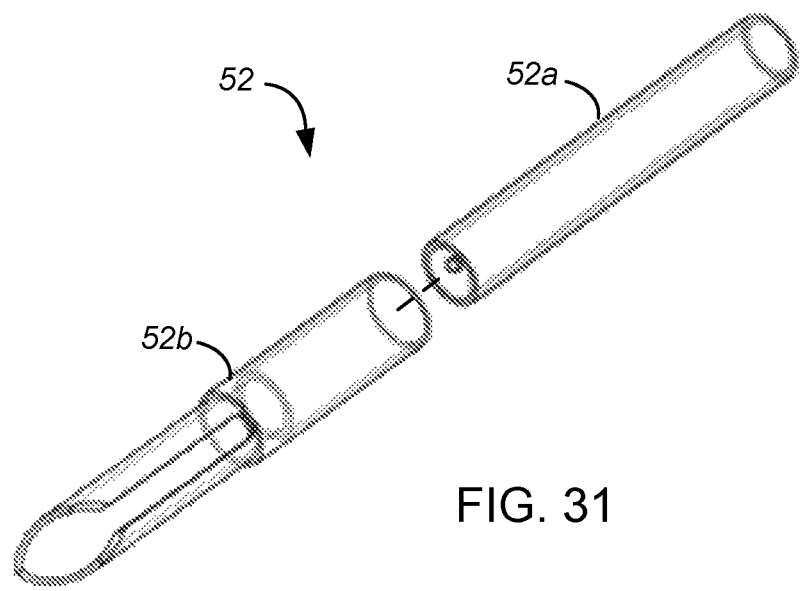
FIG. 31 illustrates a perspective view of one embodiment of a tip assembly where a cutting sheath has a segment that can be attached to the nose assembly by the end user.
Figure 32:
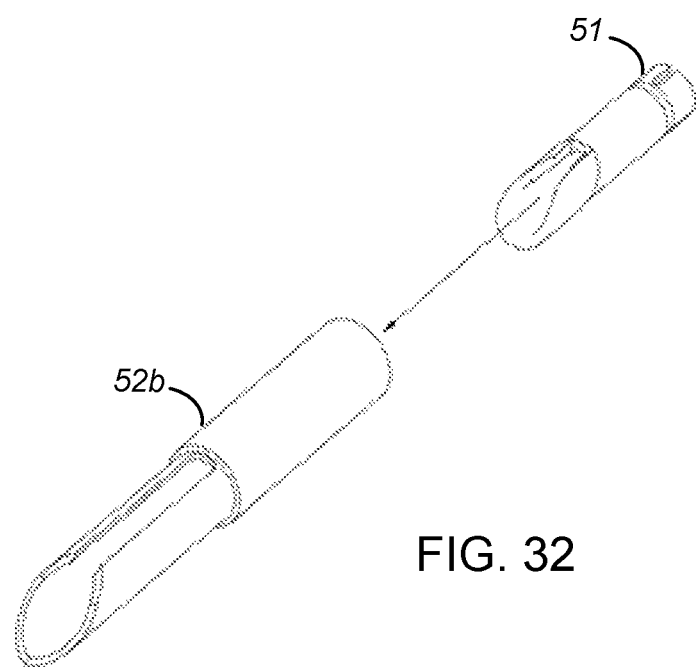
FIG. 32 illustrates a perspective view of another embodiment of a tip assembly where the cutting sheath has a segment which can be attached to the nose assembly by the end user and the ventilation tube is loadable from the back of the cutting sheath.

FIG. 31 illustrates a tip assembly for an inserter device, such as inserter device 60, where cutting sheath 52 can be attached to an actuated element assembled to distal portion 43 of inserter device 60, allowing an end user to apply cutting sheath 52 at any angular orientation that they prefer. In other words, cutting sheath 52 is broken into two parts 52a and 52b. Part 52a stays assembled to distal portion 43 of inserter device 60, and part 52b is a removable segment that can be attached to part 52a by the end user. Part 52b could be attached to part 52a and then have a ventilation tube loaded, or part 52b could be provided pre-loaded with a ventilation tube. The connection between part 52b and part 52a could be with a friction fit, similar to a luer-style connection, or it could be mechanical in nature, such as a snap fit. The connection could be permanent, or could be removable, for example to allow two pre-loaded removable sheath assemblies to be alternately attached to a single handle/nose assembly to allow bilateral treatment of two ears. FIG. 32 illustrates a ventilation tube exploded from sheath element 52b, but if assembled would be pre-loaded at the proximal end of the cutting sheath to allow a rear loading of ventilation tube. The ventilation tube illustrated in FIG. 32 shows a lateral flange 51 folded down as it would be during a 'rear loading' of the tube into sheath element 52b. This tube could also include the lateral flange shown on tube 44A, which would be constrained during tube loading, but then would return to its normal unconstrained state by extending through the slot in 52b to provide a visual depth marker.

Figure 33:
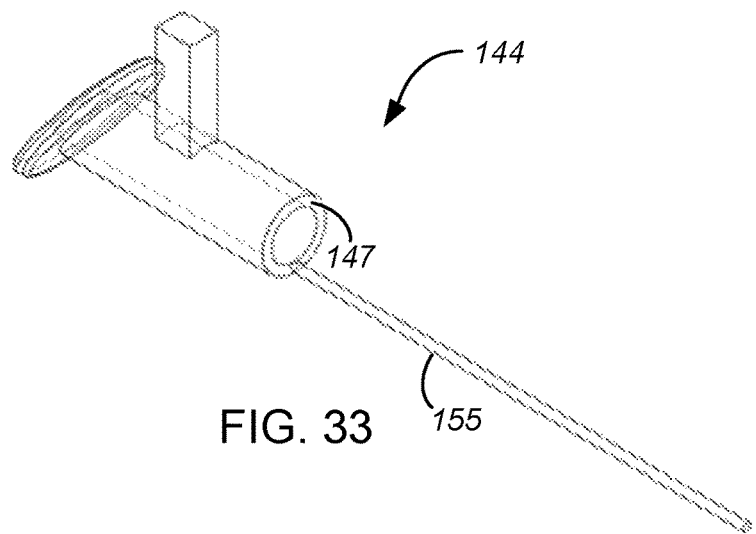
FIG. 33 illustrates a ventilation tube with an extended element to aid in pulling into a cutting sheath for loading or reloading.

FIG. 33 illustrates a ventilation tube 144 with an element 155 to pull tube 144 into an inserter device without the need for an additional tool. Element 155 extends from a proximal end 147 of tube 144. Pulling element 155 could also serve as a tether for retrieval in instances where a tube is inserted too deeply into the middle ear. Pulling element or tether 155 could be integrally part of tube 144 (i.e. molded as part of it), or an added element like a wire or a string. Pulling element 155 could also be left in place after the tube is inserted, or it could be temporary, intended to be removed after loading of the tube into the inserter, or after insertion of the tube into the eardrum.

Figure 34:
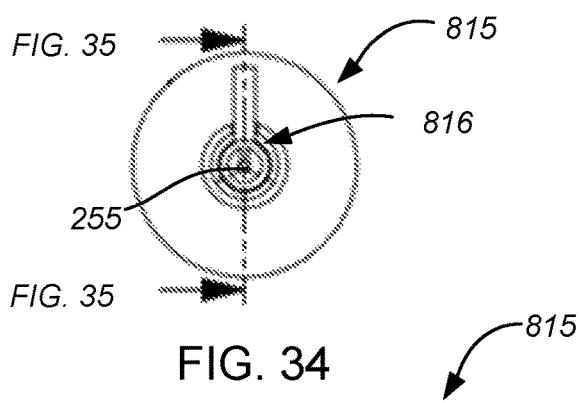
FIG. 34 illustrates an end view of a loading tool incorporating an internal loading element according to one embodiment.
Figure 35:
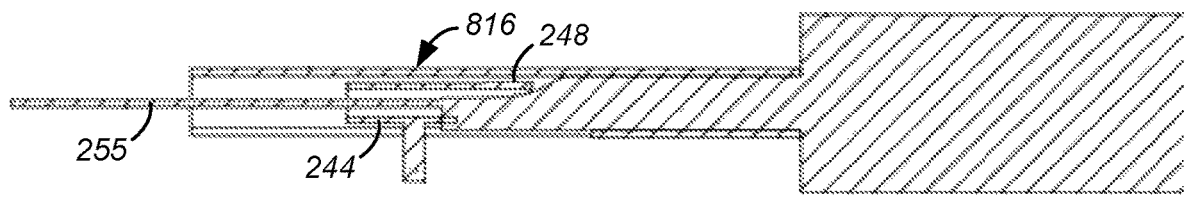
FIG. 35 is a section view of the loading tool illustrated in FIG. 34.

FIG. 34 illustrates an enlarged end view of a loading device 815 according to yet another embodiment. FIG. 35 illustrates a partial section view of loading device 815 taken through the lines indicated in FIG. 34. As illustrated, loading device 815 includes a loading jig 816 to constrain medial flange 248 or flanges and an internal element 255 to support and guide ventilation tube 244 into a cutting sheath of an inserter device. Internal element 255 may be an integral element of loading device 815 that extends axially along loading jig 816, for example an injection molded element, or it could be a standalone third element assembled to loading jig 816, for example by overmolding or otherwise joining.

Figure 36:
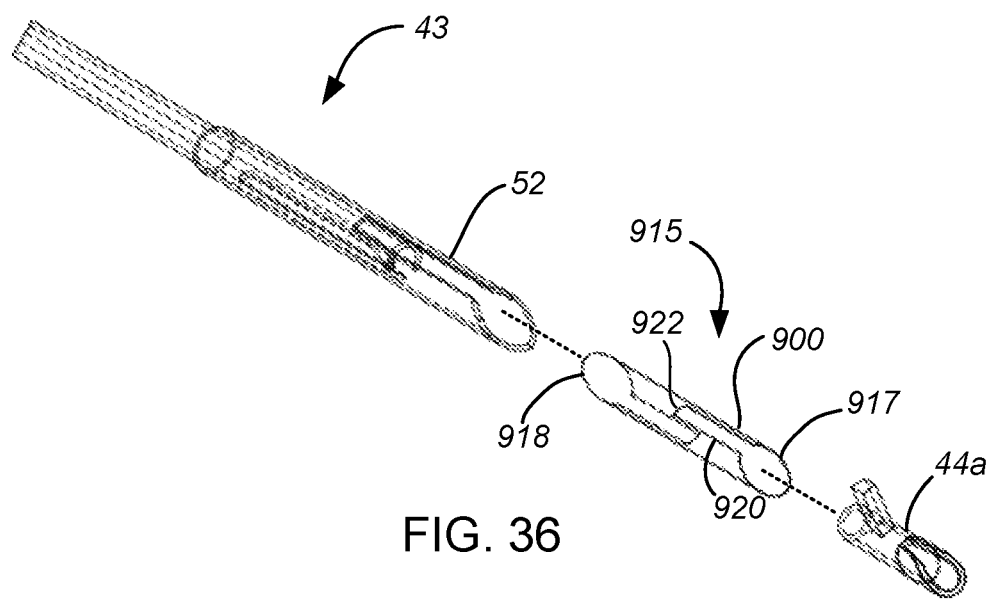
FIG. 36 illustrates an exploded perspective view of a cartridge loading system including a portion of an inserter device, a cartridge and a ventilation tube according to one embodiment.
Figure 37:
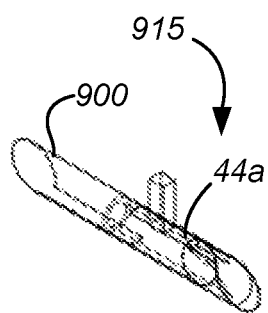
FIG. 37 illustrates a perspective view of the ventilation tube in FIG. 36 assembled into the cartridge in FIG. 35.
Figure 38:
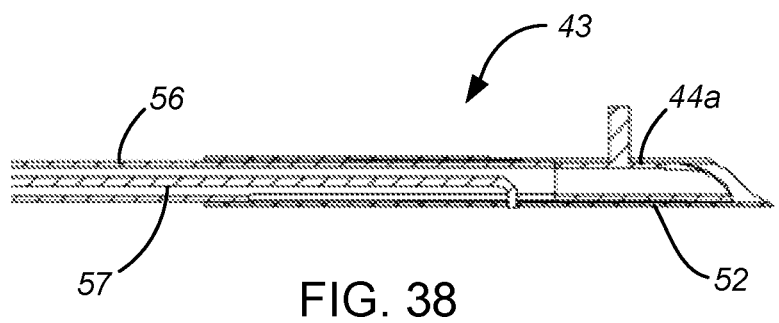
FIG. 38 illustrates a section view of the portion of the inserter device in FIG. 36, the cartridge in FIG. 36 and the ventilation tube in FIG. 36 all assembled together.

FIG. 36 illustrates a perspective view of a loading device 915 according to yet another embodiment and comprised of a cartridge 900 and ventilation tube 44a exploded therefrom with a distal end of distal portion 43 of an inserter device in position to be loaded with ventilation tube 44a. FIG. 37 shows loading device 915 that incorporates a pre-loaded cartridge 900 containing ventilation tube 44a constrained in the non-deployed state. FIG. 38 illustrates a partial section view of distal portion 44 of an inserter device after ventilation tube 44a is loaded. Cartridge 900, in the embodiment illustrated, includes a first end 917, a second end 918 and a medial slot 920 for interfacing with second end 918 is beveled to facilitate insertion into cutting sheath 52 of distal portion 43 of the inserter device. Second end 918 includes a slotted interface to insure proper alignment with an activation wire 57 within the tip assembly. The outside diameter of cartridge 900 is slightly less than the inside diameter of cutting sheath 52 while the inside diameter of cartridge 900 is slightly larger than the outer diameter of positioning rod 56, allowing the cartridge to pass thru the gap between sheath 52 and rod 56, loading the tube into the sheath. Cartridge 800 can be made from a variety of materials to provide a very thin walled vehicle but with adequate strength to maintain the constrained or compressed ventilation tube 44a. Such material may include but is not limited to a polyamide. Cartridge 800 is placed in cutting sheath 52 to a position where ventilation tube 44a resides in the proper deployment position. Then cartridge 800 is removed by moving it further inside hollow cutting sheath 52 to a remote lateral position from ventilation tube 44a, or by completely removing it as illustrated in FIG. 38. In one embodiment, cartridge 800 has a slit or tear-slot that allows the cartridge to be fully removed past any cutting sheath 52 attachment means by advancing it laterally out of the back of the cutting sheath.

Based upon the above discussion and illustrations, those skilled in the art will readily recognize that various modifications and changes may be made to the present invention without strictly following the exemplary embodiments and applications illustrated and described herein. Such modifications do depart from the true spirit and scope of the present invention, including that set forth in the following claims.

What is claimed is:

1. A system configured to load a ventilation tube into an inserter device, the system comprising:
    a loading device including:
        a main body;
        at least one solid protruding member extending from the main body and terminating at a loading tip;
        at least one elongated hollow body having a first end, an inner wall and an outer wall, wherein the elongated hollow body surrounds the protruding member such that at least a portion of an outer facing surface of the protruding member engages with an inner wall of the elongated hollow body; and
    at least one ventilation tube that engages with the loading tip of the protruding member and is at least partially located within the elongated hollow body.

2. The system of claim 1, wherein the main body comprises a first end and an opposing second end and wherein the at least one protruding member comprises a first protruding member extending from the first end of the main body and a second protruding member extending from the second end of the main body.

3. The system of claim 2, wherein the at least one elongated hollow body comprises a first elongated hollow body that surrounds the first protruding member and a second elongated hollow body that surrounds the second protruding member and wherein the at least one ventilation tube comprises a first ventilation tube engaged with the loading tip of the first protruding member and located at least partially within the first elongated hollow body and a second ventilation tube engaged with the loading tip of the second protruding member and located at least partially within the second elongated hollow body.

4. The system of claim 1, wherein the elongated hollow body comprises a non-opaque material.

5. The system of claim 1, wherein the elongated hollow body comprises a slot that extends through the inner and outer walls of the elongated hollow body and from the first end of the elongated hollow body to a terminating end spaced apart from the first end of the elongated hollow body.

6. The system of claim 5, wherein the ventilation tube comprises at least one lateral flange extending outwardly from an outer wall of the ventilation tube and protrudes through the slot in the elongated hollow body.

7. The system of claim 1, wherein the ventilation tube comprises at least one medial flange extending outwardly from an outer wall of the ventilation tube and is constrained inside the elongated hollow body, wherein the medial flange engages with the loading tip of the protruding member.

8. The system of claim 7, further comprising an inserter device having a distal end that is configured to be inserted through the first end of the elongated hollow body of the loading device and under the medial flange of the ventilation tube so that a friction between the inner wall of the elongated hollow body and the medial flange is replaced by a friction between the distal end of the inserter device and the medial flange so that the ventilation tube is loaded inside the distal end of the inserter device.

9. The system of claim 7, further comprising an inserter device having a distal end, wherein the ventilation tube is held in place inside the elongated hollow body of the loading device and the at least one solid protruding member of the loading device is movable through the elongated hollow body to push the ventilation tube out of the elongated hollow body and into the distal end of the inserter device.

10. A system configured to load a ventilation tube into a distal end of an inserter device, the loading system comprising:
    a loading tool including:
        a main body and at least one protruding member extending from the main body and terminating at a loading tip;
        at least one elongated hollow body having a first end an inner wall and an outer wall, wherein the at least one protruding member is inserted through the first end of the elongated hollow body such that an outer facing surface of the at least one protruding member slidingly engages with an inner wall of the elongated hollow body;
    a ventilation tube being held at least partially in place inside the elongated hollow body and having a medial end and a lateral end, wherein the medial end of the ventilation tube is in direct contact with an edge of the loading tip of the at least one protruding member and wherein the medial end is defined as being an end of the ventilation tube configured to be located nearer to a midline of the patient than the lateral end; and
    an inserter device having a distal end, wherein the distal end is slid through the first end of the at least one elongated hollow body to load the ventilation tube inside the distal end of the inserter device.

11. The loading system of claim 10, wherein the elongated hollow body comprises a slot that extends through the inner and outer walls, wherein a lateral flange on the ventilation tube protrudes through the slot when the elongated hollow body is configured to hold the ventilation tube in place inside the elongated hollow body.

12. The loading system of claim 11, wherein the slot in the elongated hollow body extends from the first end of the elongated hollow body to a terminating end spaced apart from the first end of the elongated hollow body.

13. The loading system of claim 10, wherein the loading tip of the protruding member is spatulate-shaped and comprises a top section having a blunt end and a bottom section having an arcuate cutout.

14. The loading system of claim 13, wherein the medial end of the ventilation tube comprises a beveled medial flange, wherein the top section of the spatulate-shaped loading tip of the protruding member engages with a top of the beveled medial flange and the bottom section of the spatulate-shaped loading tip of the protruding member engages with a bottom of the beveled medial flange.

15. The loading system of claim 14, wherein a portion of the distal end of the inserter device slides under the bottom of the beveled medial flange to load the ventilation tube inside the distal end of the inserter device.

16. The loading system of claim 10, wherein the at least one protruding member of the loading tool is movable through the elongated hollow body so the at least one protruding member pushes the ventilation tube out of the elongated hollow body and into the distal end of the inserter device.

17. A method of loading a ventilation tube into a distal end of an inserter device, the method comprising:
  locating a ventilation tube at least partially inside a hollow tubular body having a first end, an inner wall and an outer wall;
  engaging a loading tip of a protruding member on a main body of a loading tool with the ventilation tube located at least partially inside the hollow tubular body;
  inserting a distal end of an inserter device through the first end of the hollow tubular body to load the ventilation tube inside the distal end of the inserter device.

18. The method of claim 17, wherein inserting the distal end of the inserter device through the first end of the hollow tubular body further comprises inserting the distal end of the inserter device under a constrained medial flange of the ventilation tube so that a friction between the inner wall of the hollow tubular body and the medial flange is replaced by a friction between the distal end of the inserter device and the medial flange so that the ventilation tube is loaded inside the distal end of the inserter device.

19. The method of claim 18, wherein inserting the distal end of the inserter device through the first end of the hollow tubular body further comprises aligning a slot in the distal end of the inserter device with a slot in the hollow tubular body, wherein a lateral flange on the ventilation tube protrudes through the slot in the hollow tubular body and through the slot in the inserter device.

20. The method of claim 19, further comprising pulling the distal end of the inserter device out through the first end of the hollow tubular body with the ventilation tube located inside the distal end of the inserter device and the lateral flange protruding through the slot in the inserter device.

21. The system of claim 1, wherein the at least one elongated hollow body extends from the main body.

22. The method of claim 17, further comprising removing the hollow tubular body from around the protruding member on the main body such that the loading tip of the protruding member is configured to be used to adjust the ventilation tube inside the distal end of the inserter device.

\* \* \* \* \*